United States Patent
Sullivan et al.

(10) Patent No.: US 9,669,176 B2
(45) Date of Patent: Jun. 6, 2017

(54) MASK

(75) Inventors: Colin Edward Sullivan, Balmain (AU); Paul Wilkie, Sydney (AU)

(73) Assignee: AUSTRALIAN CENTRE FOR ADVANCED MEDICAL TECHNOLOGY LTD., Sydney, New South Wales (AU)

( * ) Notice: Subject to any disclaimer, the term of this patent is extended or adjusted under 35 U.S.C. 154(b) by 1472 days.

(21) Appl. No.: 12/698,307

(22) Filed: Feb. 2, 2010

(65) Prior Publication Data
US 2010/0192954 A1    Aug. 5, 2010

Related U.S. Application Data

(63) Continuation-in-part of application No. 10/111,978, filed as application No. PCT/AU00/01349 on Nov. 3, 2000, now abandoned.

(30) Foreign Application Priority Data

Nov. 3, 1999    (AU) ...................................... PQ3822

(51) Int. Cl.
*A61M 16/06*    (2006.01)

(52) U.S. Cl.
CPC ........ *A61M 16/06* (2013.01); *A61M 16/0616* (2014.02); *A61M 16/0683* (2013.01); *A61M 2210/0618* (2013.01)

(58) Field of Classification Search
CPC ....... A61M 16/06–16/0655; A61M 2016/0661
(Continued)

(56) References Cited

U.S. PATENT DOCUMENTS 4,782,832 A    11/1988 Trimble et al.
4,809,692 A *   3/1989 Nowacki et al. ........ 128/206.24
(Continued)

FOREIGN PATENT DOCUMENTS

AU    199942476    11/1999
JP    52-76695 U    6/1977
(Continued)

OTHER PUBLICATIONS

"Lighten up" Respironics brochure (1999).
(Continued)

*Primary Examiner* — LaToya M Louis
(74) *Attorney, Agent, or Firm* — Browdy and Neimark, PLLC

(57) ABSTRACT

A mask for supplying gas under pressure to the nasal airway of an infant human includes a manifold for supplying air to an aperture in the mask. A shaped membrane structure formed from a thin walled membrane defines an enclosure for receiving at least the nares of an infant human nose and a generally trapezoidal aperture adapted to fit around the nasal area of the infant human. Part of the membrane around the aperture is sufficiently flexible to mold to the shape of the infant human's nasal area or is contoured to generally match the contours around that nasal area while the membrane structure itself has sufficient rigidity to support the weight of the backing plate without collapsing. The provision of a generally trapezoidal rather than the generally triangular apertures for fitting around the nares provides a substantially improved fit when the mask is used with infants. The molding or contouring of the membrane structure around the aperture to match the shape of the infant's facial contours around the nasal area including the provision of a generally planar portion surrounding the aperture is also important in ensuring a comfortable fit and an effective seal. The mask is (Continued)

entirely formed from a flexible elastomeric material for reason of comfort and function.

19 Claims, 13 Drawing Sheets

(58) Field of Classification Search
USPC ............ 128/202.27, 204.18, 205.25, 206.21,
128/206.24–206.28, 207.11, 207.13,
128/207.18
See application file for complete search history.

(56) References Cited

U.S. PATENT DOCUMENTS

| | | | |
|---|---|---|---|
| 5,243,971 A | 9/1993 | Sullivan et al. | 128/205.25 |
| 5,419,317 A | 5/1995 | Blasdell et al. | |
| 5,542,128 A | 8/1996 | Lomas | 2/173 |
| 5,560,354 A | 10/1996 | Berthon-Jones et al. | |
| 5,647,357 A | 7/1997 | Barnett et al. | 128/206.24 |
| 5,657,752 A | 8/1997 | Landis et al. | |
| 5,662,101 A | 9/1997 | Ogden et al. | 128/205.25 |
| 5,687,715 A | 11/1997 | Landis et al. | 128/207.18 |
| 5,746,201 A | 5/1998 | Kidd | 128/206.24 |
| 5,768,715 A * | 6/1998 | Gregg et al. | 2/411 |
| 5,921,239 A | 7/1999 | McCall et al. | |
| 5,951,504 A * | 9/1999 | Iglesias et al. | 602/27 |
| 6,012,455 A | 1/2000 | Goldstein | |
| 6,019,101 A | 2/2000 | Cotner et al. | |
| 6,039,044 A | 3/2000 | Sullivan | |
| 6,044,844 A | 4/2000 | Kwok et al. | |
| 6,098,201 A * | 8/2000 | Boros, Sr. | 2/206 |
| 6,112,746 A | 9/2000 | Kwok et al. | 128/207.13 |
| 6,119,694 A * | 9/2000 | Correa et al. | 128/207.13 |
| 6,192,886 B1 | 2/2001 | Rudolph | 128/207.13 |
| 6,357,441 B1 | 3/2002 | Kwok et al. | 128/207.13 |
| 6,467,483 B1 | 10/2002 | Kopacko et al. | 128/207.12 |
| 6,581,602 B2 | 6/2003 | Kwok et al. | 128/207.13 |
| 6,615,832 B1 | 9/2003 | Chen | 128/206.26 |
| 6,626,177 B1 * | 9/2003 | Ziaee | 128/206.21 |
| 6,634,358 B2 | 10/2003 | Kwok et al. | 128/205.25 |
| 6,712,072 B1 | 3/2004 | Lang | 128/206.27 |

FOREIGN PATENT DOCUMENTS

| | | |
|---|---|---|
| WO | 98/18514 | 5/1988 |
| WO | WO 96/17643 | 6/1996 |
| WO | WO 99/43375 | 9/1999 |

OTHER PUBLICATIONS

"Data Management Software 3.0" Encore; Respironics (2000).
"Rise and Shine" Sleep Apnea Solutions brochure; Respironics.
"Encore SmartCard"; Respironics.

* cited by examiner

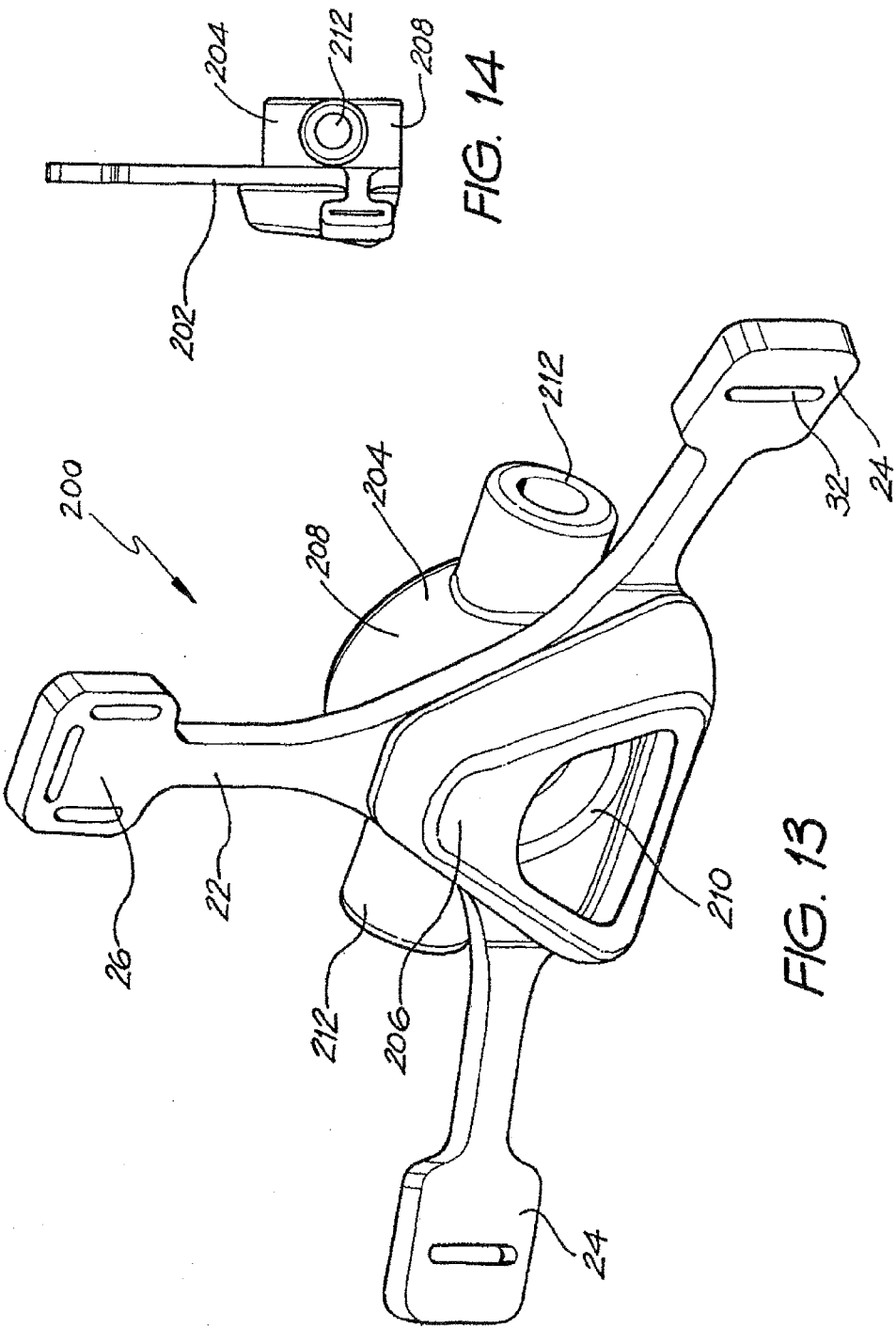

MASK

CROSS REFERENCE TO RELATED APPLICATIONS

This application is a continuation-in-part of U.S. patent application Ser. No. 10/111,978 now abandoned, filed Aug. 25, 2002 which was the US national phase of International Patent Application No PCT/AU00/1349, filed 3 Nov. 2000, which claims priority from Australian provisional application No PQ 3822, filed 3 Nov. 1999, the entire content of all the above-mentioned applications being hereby incorporated by reference.

FIELD OF THE INVENTION

This invention relates to a mask for supplying gases, typically air or oxygen to the airways of humans. The mask is particularly, but not exclusively, suited to infants, neonates, and premature neonates.

BACKGROUND OF THE INVENTION

Various masks are used to provide fresh air or oxygen to the airways of humans. A specialised category of masks is used to provide positive pressure to the human airway. Positive pressure applied in this manner has two different goals.

In a first category, positive pressure is applied to the lungs for the purpose of stabilising the lungs, and in particular for maintaining a minimum inflation level of the small air spaces in which gas transfer occurs (the alveoli). This therapy is very useful in patients with a variety of lung diseases, where the disease processes tend to lead to collapse (closure of the airway containing regions of the lung).

In a second category, the positive pressure is applied to the nasal airway with the intention of maintaining the pressure in, and the patency of, the upper airway. This form of positive airway pressure is known as nasal continuous positive airway pressure (nasal CPAP). This is now the "gold standard" treatment for the condition known as obstructive sleep apnea (OSA), and also for snoring and a variant of this therapy, bi-level positive pressure, is used to both stabilise the upper airway and provide additional positive pressure to support breathing. Obstructive sleep apnea is a condition in which the upper airway closes in sleep, and does so repeatedly. Nasal CPAP, when applied for the duration of sleep, stabilises the upper airway and allows for normal sleep and normal breathing.

The use of nasal continuous positive airway pressure to treat upper airway obstruction in sleep has been the subject of patents, and has been referred to in a variety of medical publications and was developed primarily for adult use. In recent years nasal CPAP has been used in the treatment of infantile obstructive apnea. However, a major problem with effectively treating an infant subject with CPAP is obtaining a mask that is appropriate for that infant. There are two issues which are critical in the effective delivery of CPAP. First, the mask must be able to maintain a known pressure in the airways during both the inspiratory and the expiratory cycle. To do so requires a hermetic seal between the mask proper and the subject's skin. Secondly, it is necessary, or at least highly desirable, to minimise and eliminate torsional movement causing twisting of the mask and consequently the leaking that arises either from movement of the subject's head, or movement of the air delivery pipe which must be attached to the mask.

The extent to which these two issues affect the use of the mask in adults as opposed to infants varies considerably. First, in the case of achieving a good seal, the adult is able to readily adjust their mask if they are experiencing a less than perfect seal (which usually results in a leak of air from the mask). In contrast, infants are unable to manage the required readjustment themselves. Secondly, problems arising from the torsional effects between the two interfaces of the air delivery pipe to the mask manifold, and the mask seal to the face are greatly exaggerated with infants as compared with adults. It is well known that a typical infant makes many more movements, particularly head movements, during sleep compared with a typical adult. In particular, the infant has many twitches and startles with concomitant head movements during dreaming sleep (rapid-eye movement sleep, known as REM). Further, the infant spends much more time in REM sleep (up to 50% of total sleep time) than the adult (less than 25% of total sleep time). Clearly the greater the number of movements, the more likely it is that the torsional effect will cause the mask to lift from the face which will lead to air leaking. Again, the adult is better able to adjust their mask to overcome this problem, than the infant.

Notwithstanding these issues, until now, infant masks have been developed on the basis of scaling down the adult mask to approximate to the infant face and nose. The problems with this scaling down process are fourfold.

First, the adult nose and middle third of the face is very different in shape from that of the infant. The adult nose is more elongated than, and protrudes far more from the surface of the face compared to the infant nose which is relatively flat, with no bridge, with the nares (nostril passages) pointing outwards. Therefore in order to fit the adult nose the base of the mask has a triangular shape elongated in the vertical axis and a "notch" region to accommodate the nose bridge. In contrast, with an infant, the width at the base of the nose approximates the height from the base of the nose (nares) to the apex of the nose (nasion). The "proportional shape" of the nasal area of an adult is rectangular and "V" shaped compared with a square and flat "proportional" shape for an infant. In addition to this basic difference in proportional shape, the adult face has quite marked contours especially around the nose and cheek area which are absent in the infant. The adult mask must therefore have acute angles which accommodate these facial contours. Thus, when an adult mask is scaled down for an infant, not only are the proportions wrong for the infant nose and face, but the angles which are unnecessarily incorporated, inadvertently introduce a new problem. Because the infant has a relatively flat nose, and virtually no bridge, the angles promote formation of channels in the sealing margin of the mask, especially in the region of the nasal bridge.

Secondly, in adult mask designs, the straps of the head harness connect with lugs on the rigid manifold of the mask in the order of 20 mm away from the surface of the face to allow the mask to accommodate the height of the adult nose. Because of this, a potential fulcrum effect is created. In the adult this fulcrum effect is not as problematic as in the infant, not only because the adult is less mobile during sleep as discussed above, but also because the contours of the adult face and cheeks can offset this rise. In the infant, when the mask used is merely a scaled down adult mask, the elevation of the strap lugs above the face is about 12 mm. This by itself creates a potential fulcrum as it does in the adult, but the effect is enhanced by the fact that there is no offset from the infant cheek due to the smaller facial area. Consequently, the straps holding the mask in place come into greater contact with the side of the face in the infant, compared to the cheek in the adult.

Thirdly, because the attachment of the paediatric mask to the face and head mimics that of the adult mask, the torsional forces are increased. The greater torsional effect is due to the decreased surface area of the mask face contact relative to the size of the air delivery pipe. Thus relatively minor movements can result in sufficient torsional forces to cause movement at the interface between the mask and the infant's face.

Fourthly, adult masks typically comprise a rigid manifold made of a hard plastic material. Straps attach to the manifold for locating the mask in position on an adult patient. The rigid manifold supports a flexible face engaging portion/seal which seals against the adults face. However such designs even if scaled down, are not suitable for infants, who may be restless during sleep. Even relatively minor movements may cause discomfort or a breakdown in sealing due to the rigid manifold contacting the infant's bed and levering the face engaging portion away from the infant's face. More serious discomfort would occur if the infant were to turn over and lie face down in which case the rigid shell would be pushed into the infant's face.

There are numerous published patents and patent applications which relate to masks for use in CPAP and for other gas supply applications. They include U.S. Pat. No. 5,243,971 (Sullivan et al), AU 42476/99 (ResMed Ltd), WO 98/18514 (Sleepnet Corp), U.S. Pat. No. 5,657,752 (Landis et al) and U.S. Pat. No. 5,650,354 (Berthon-Jones et al) which describes a combined mouth and nasal mask. These all rely on a rigid manifold and a flexible face engaging portion/seal.

All of those publications are directed to masks for adults and it is significant to note that despite nasal CPAP having been in use on infants for over twenty years no satisfactory infant mask has yet been proposed. For this reason many clinicians have preferred to use nasal prongs for undertaking nasal CPAP in infants. In spite of nasal prongs often being uncomfortable for infants, this preference has been due to the prongs' ability to provide an adequate gas seal together with the lack of an effective alternative nasal interface product.

It is an object of the present invention to alleviate some or all of the above mentioned problems with the prior art and provide an improved mask which is particularly suited for infant facial structures. For the purposes of this specification the term infant or infant human includes premature/neonatal babies, newborn babies, infants and small children having infant facial profiles who may be older than one year, possibly aged up to eighteen months to about two years old. The shape of the infant's face is the significant factor, not the age of the child.

SUMMARY OF THE INVENTION

Thus in a first broad aspect of the present invention, there is provided a mask for supplying gas under pressure to the nasal airway of a human, including:

a manifold for supplying air to an aperture in the mask:

a support structure or plate for supporting the manifold; and a shaped membrane structure formed from a thin walled membrane extending generally away from the support structure, the shaped membrane structure defining an enclosure for receiving at least the nares of an infant human nose and a generally trapezoidal aperture adapted to fit around the nasal area of the infant human wherein part of the membrane around the aperture is sufficiently flexible to mould to the shape of the infant human's nasal area or is contoured to generally match the contours around that nasal area whilst the membrane structure itself has sufficient rigidity to support the weight of the support structure or plate without collapsing.

The provision of a generally trapezoidal aperture rather than the generally triangular apertures for fitting around the nares provides a substantially improved fit when the mask is used with infants. The moulding or contouring of the membrane structure around the aperture to match the shape of the infant's facial contours around the nasal area is also important in ensuring a comfortable fit and an effective seal.

Typically the generally trapezoidal aperture can be notionally located inside an isosceles trapezium with the aperture having a base edge, side edges and a top edge touching the notional isosceles trapezium. The top edge of the generally trapezoidal aperture will typically be gently curved convexly as will the base edge of the aperture although typically relatively less curved than the top edge. These top and base edge curves will typically be symmetrical about the central vertical axis of the notional isosceles trapezium. In all cases the notional isosceles trapezium top and bottom edges will touch the top and bottom edges of the generally trapezoidal aperture at the respective centre points of the top and bottom edges of the isosceles trapezium. The top and bottom edges of the notional isosceles trapezium will typically be tangential to the top and bottom edges of the aperture at the centre points of the notional isosceles trapezium's edges. In all cases the side edges of the notional isosceles trapezium will be tangential to the sides edges of the aperture at the midpoint of the trapezium side edges.

The isosceles trapezium typically defines angles between its base and sides of 55 to 65 degrees most preferably about 60 degrees and the ratio of the length of the top of the notional isosceles trapezium to the length of its base is between about 1 to 1.8 to about 1 to 3 and most preferably 1 to 2.4.

It is to be recognised that small variations in the curvature of the side edges and top and bottom edges of the generally trapezoidal aperture are allowable. For instance these side edges could all be straight or could have a curvature that is slightly concave. In the case where the aperture side edges were slightly concave then the notional trapezium would fit slightly within the generally trapezoidal aperture. However, in all cases, the notional isosceles trapezium may be uniquely described by each unique embodiment of the generally trapezoidal aperture as outlined above.

In a particularly preferred embodiment, the support structure/plate (manifold backing plate) and shaped membrane structure are generally flexible enough so that they will slightly distort if the infant pushes the mask against a hard surface such as a bed or pillow. The flexibility will enable the mask body to slightly distort without the shaped membrane lifting off the infants face thereby breaking the gas seal causing gas leakage. This solves the problem where an infant using a mask with a rigid manifold pushes it against a hard surface causing discomfort and or gas leakage.

In a particularly preferred embodiment, the backing plate is generally triangular in shape.

Typically, the thickness of the membrane will diminish from the backing plate to the aperture. The membrane may be about 1.2 mm thick adjacent the backing plate but only 0.2 mm thick at the aperture.

It is preferred that the backing plate is flexible.

Typically, a flexible arm extends away from the backing plate at or adjacent each of the three apexes of the triangular plate.

It is preferred that a pad is defined at the end of each flexible arm distal from the plate.

In a particularly preferred embodiment, the manifold, the pads, arms, membrane and backing plate are all integrally moulded from a flexible elastomeric material, most preferably a high tear resistant silicone elastomer such as Silastic (Registered Trade Mark of the Dow Corning Corporation) or Santoprene (Registered Trade Mark of the Monsanto Co.) at a thickness of between 3 to 6 mm, typically 3.5 mm for the body of the mask but decreasing to as thin as 0.2 mm at the edge of the face contacting membrane aperture.

The moulding of the backing plate and arms from a flexible elastomeric material, enables the arms to flex at the point where they meet the backing plate. This obviates the problems of the prior art in which rigid arms extend away from the mask (to which are attached straps) which increases the torque applied to the mask. The mask of the present invention, also allows the straps to pass over the infant's cheeks, rather than down the side of their heads. That provides a more secure fit of the mask and makes the mask less likely to move.

For a mask for a typical three month old infant, the base of the triangle forming the backing plate will be approximately 40 mm long with the height of the triangle around 35 mm. The membrane will typically extend around 10 to 14 mm, typically 12 mm away from the backing plate. The notional isosceles trapezium surrounding the generally trapezoidal aperture in the membrane will have a base of around 20 to 25 mm and a height of around 10 to 15 mm and a top which is approximately 12 mm long and which is preferably slightly curved.

For a mask for a typical twelve month old infant the membrane will typically extend around 12 to 16 mm, typically 14 mm away from the backing plate. The notional isosceles trapezium surrounding the generally trapezoidal aperture in the membrane will have a base of around 40 to 45 mm and a height of around 18 to 25 mm and a top which is approximately 16 mm to 19 mm long. The top of the aperture is preferably slightly curved.

It is to be understood that masks for premature or newborn infants will have smaller dimensions than those for the three month old infants.

In a particularly preferred embodiment, the plane of the arms is offset from the plane of the backing plate by around 10 to 25°, such that when the mask is placed over the nasal area of an infant human the arms tend to extend downwardly onto the cheeks of the infant. Preferably as well as the offset from the plane of the backing plate, those arms which extend towards the cheeks of the infant also extend down the infants face so as provide a force vector (when the strap is attached to a head harness) which tends to pull the mask down from the nose bridge preventing the mask from moving up in that direction. Infants tend to move their head from side to side, which tends to cause existing masks to ride up the infant's face towards their forehead. The preferred embodiment described above addresses this problem.

The arms may be attached to an infant or human face by use of skin adhesive. Alternatively, the pads may be connectable to straps attached to a cap. These straps could be connected to the pads by fastening materials such as velcro or the like.

Typically, a number of small holes will be defined on the manifold to provide a constant leak to atmosphere and thus a way out for expired air. The number and size of the holes are determined by the pressure of air supplied to the mask and flow delivery system and are chosen to enable the desired pressure and air flow through the mask.

In one embodiment of the invention, the mask is provided in two detachable parts.

The separation of the mask system into two detachable parts, readily allows for the first part or applicator to be put in place around the nose of an infant and to be held in place with or by adhesive or by straps and a cap. The infant or child can then be allowed to sleep without the presence of air pressure and air flow coming into the nasal region. Thus the applicator can be used as a trainer to get the child or infant used to the mask. Further, once the infant or child is asleep, the parent or carer can then snap connect the air delivery to the applicator completing the formation of a fully operational CPAP mask or pressure support ventilation mask.

In a particularly preferred embodiment, engagement between the two detachable parts is by means of a generally tubular projection fitting inside a generally cylindrical hole, the hole being provided on the manifold and the tube on the backing plate, or vice versa.

It is preferred that one of the hole and the projection is generally elliptical so that compression of the ellipse into a circle can be used for inserting the projection into the hole such that when the ellipse is relaxed, it will return to its original shape and retain the projection in the hole.

In an alternative embodiment, the manifold is integral with the backing plate, but the structure is such that the manifold extends along one of the arms of the mask, typically the arm which extends from the mask towards the patient's forehead, in use.

Preferably the manifold extends to one distal end of one of the arms where a port or hole for receiving an air delivery pipe is provided.

The provision of the air port at the end of one of the arms of the mask greatly reduces the torsion effects on the mask due to the air delivery pipe.

The manifold may be made of a thin flexible material and include a series of hoops or strengthening rings to assist the membrane in maintaining the shape of the manifold. The arm and manifold are then sufficiently flexible to absorb some of the movement of the mask relative to the delivery pipe.

The present invention also encompasses a method of supplying gas to the airway of a human using any of the embodiments of the invention described above.

Typically the method will be used to supply oxygen or air to the airway for nasal CPAP, or nasal ventilation or nasal pressure support.

In a particularly preferred embodiment the outer surface of the shaped membrane structure extending from and immediately adjacent to the mask aperture is of a generally planar shape. This includes the sides and bottom of this surface extending perpendicularly out along the surface from the aperture by approximately 1 mm to 4 mm from the sides and bottom edges of the aperture respectively, and the top of this surface extending perpendicularly out along the surface from the aperture by approximately 4 mm to 10 mm from the top edge of the aperture. These dimensions will vary depending on the size of the mask which may be designed to fit infant faces from premature babies to approximately 12 month old infants or older. In this embodiment the mask is designed so that this outer surface shape closely approximates to that of the contours of the facial surface against which it sits when in use. In this embodiment this portion of the outer surface of the shaped membrane can be placed on a planar surface resulting in no point of the shaped membrane outer surface being perpendicularly more than 5 mm from the planar surface. In the example of a mask designed for use by three month old infants this maximum distance dimension is approximately 3 mm. In addition the angle formed between a line drawn tangentially to this section of the outer membrane surface and perpendicularly to the aperture outline tangent, and the planar surface is typically never larger than 20 degrees. For instance in a mask designed for use with three month old infants the largest angle found, around the entire aperture of the outer membrane surface, to the planar surface is approximately 12 degrees while the smallest angle is approximately 4 degrees. The embodiment allows the mask shape to be a best fit to the facial contours of typical infants. In contrast typical masks designed to fit adults are not generally planar. Portions of the typical adult mask surface section described above will typically be significantly more than 5 mm from the best fit surface plane and or the angle between the membrane and planar surfaces will be significantly more than 20 degrees at some point around the mask aperture. In some adult masks portions of the mask surface section will be over 10 mm from the surface plane and the mask surface angle over 45 degrees.

BRIEF DESCRIPTION OF THE DRAWINGS

The invention will now be described by way of example only and with reference to the accompanying drawings in which:

FIG. 13 is an isometric view of a third embodiment of a mask to fit the nasal area of a three month old infant;

FIG. 14 is a side view of the mask of FIG. 13; and

DETAILED DESCRIPTION OF PREFERRED EMBODIMENTS

Figure 1:
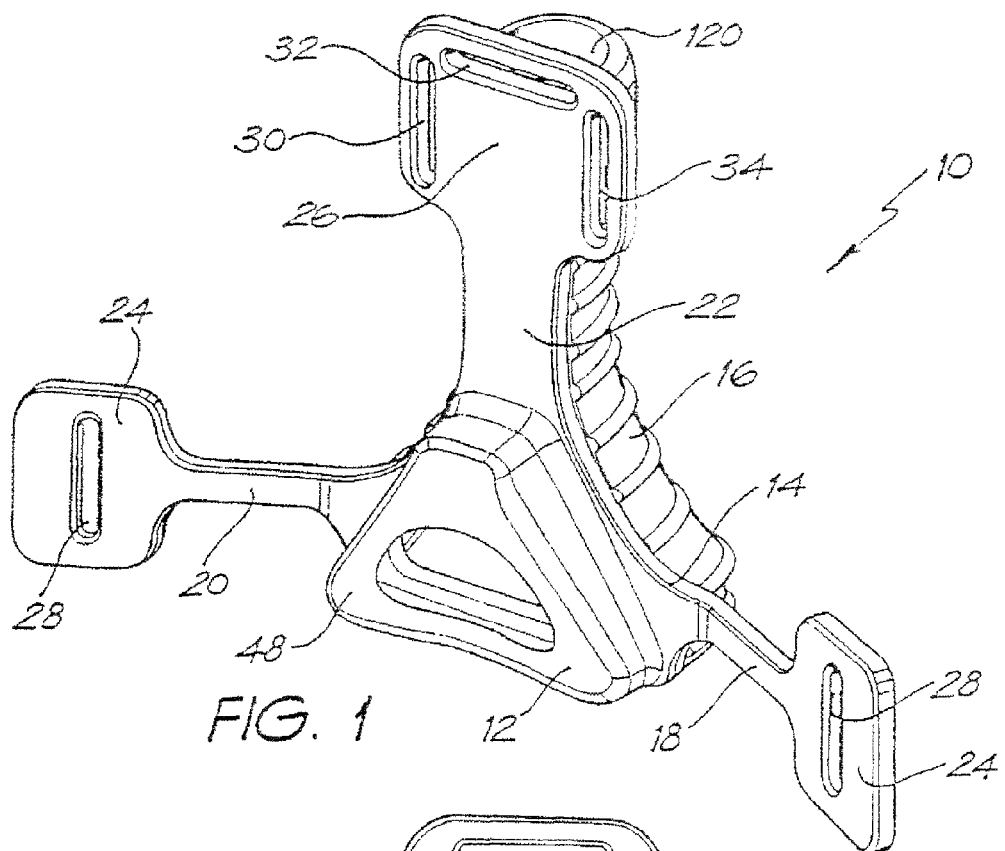
FIG. 1 is an isometric view of a first embodiment of a mask to fit the nasal area of a three month old infant for supplying air at a positive pressure to the infant's nasal airways.

Referring to the drawings, FIG. 1 shows a mask 10 suitable for use on three month old infants. In the described embodiment the mask is made from three moulded components a shaped membrane structure 12, a support structure 14 in the form of a combined support or backing plate and arms 14 and a manifold 16 which are glued together, although other constructions are possible. The components of the mask are preferably made from Silastic (Registered Trade Mark of the Dow Corning Corporation). However, other flexible and/or elastomeric materials could be used. In a particularly preferred embodiment the mask may be moulded (e.g. injection moulded) in one piece rather than assembled from separately moulded components.

The centre of the support structure is a generally triangular plate from which three arms 18, 20 and 22 extend. The support structure is about 4 mm thick and is flexible but will retain its shape and is not floppy.

Figure 2:
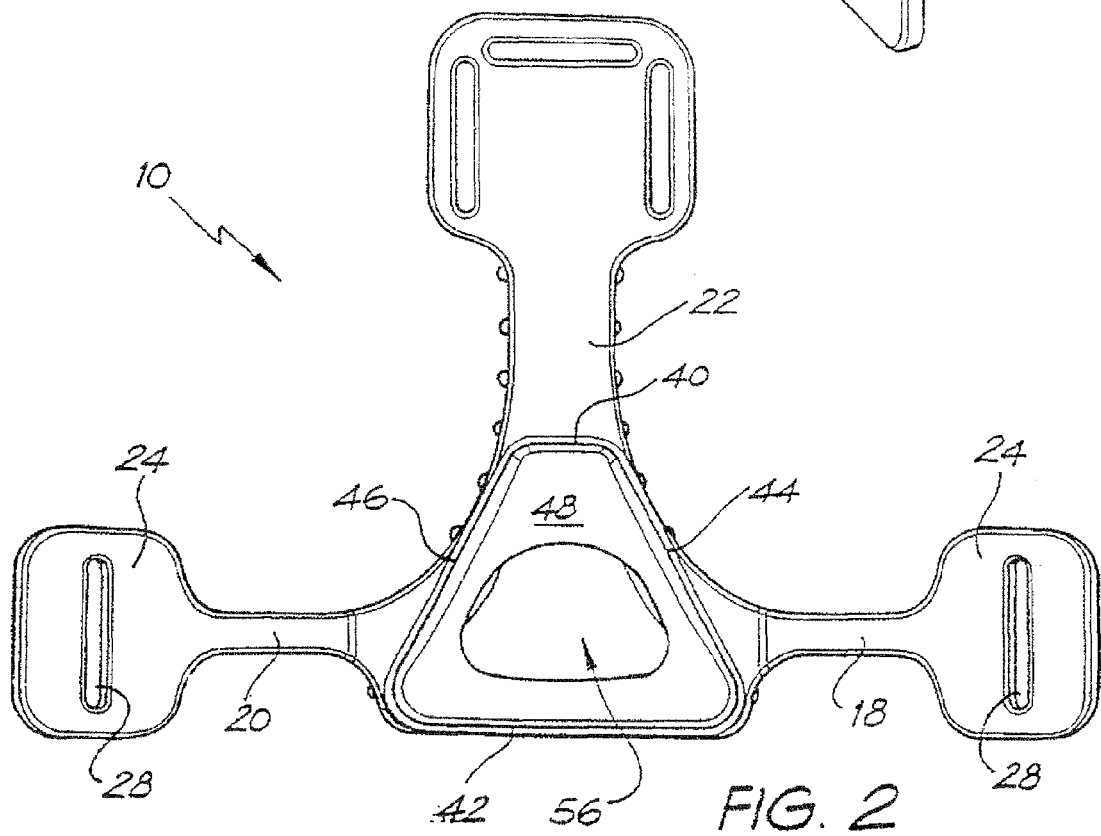
FIG. 2 is a front view of the mask shown in FIG. 1.
Figure 15:
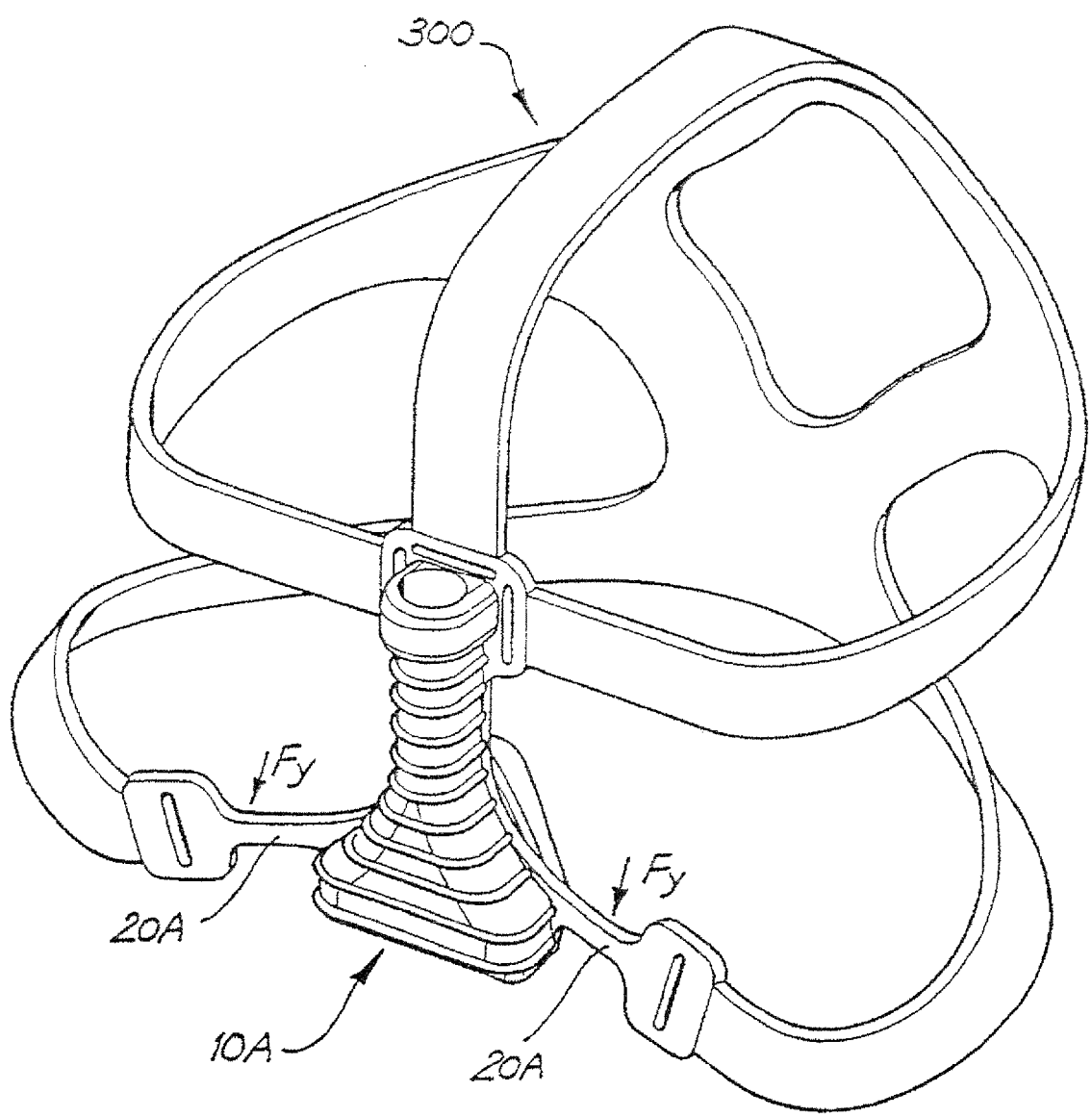
FIG. 15 is an isometric view of a variant of the mask of FIG. 1 fitted to a harness.

One of the arms 22 extends away from the apex at the top of the triangular plate and is about 40 mm long and is wider than the other two arms 18 and 20 which extend away from the triangular plate adjacent each of the two apexes at the base of the triangular plate as oriented in FIGS. 1 and 2. At the end of each of the two arms 18, 20, there is a rectangular pad 24 measuring approximately 15×17 mm. A relatively larger pad 26 is defined at the end of arm 22. Each pad 24 defines a slot 28. The larger pad 26 includes three slots 30, 32, 34. The slots 28, 30, 32, 34 are provided to allow a head harness to be attached to the mask 10 for securing the mask 10 in place on an infant's face. FIG. 15 illustrates this with a variant of the mask 10 shown in FIG. 1. As discussed above, the pads 24, 26, arms 18, 20, 22 and triangular plate of the support structure 14 are all preferably integrally moulded in one component.

Figure 3:
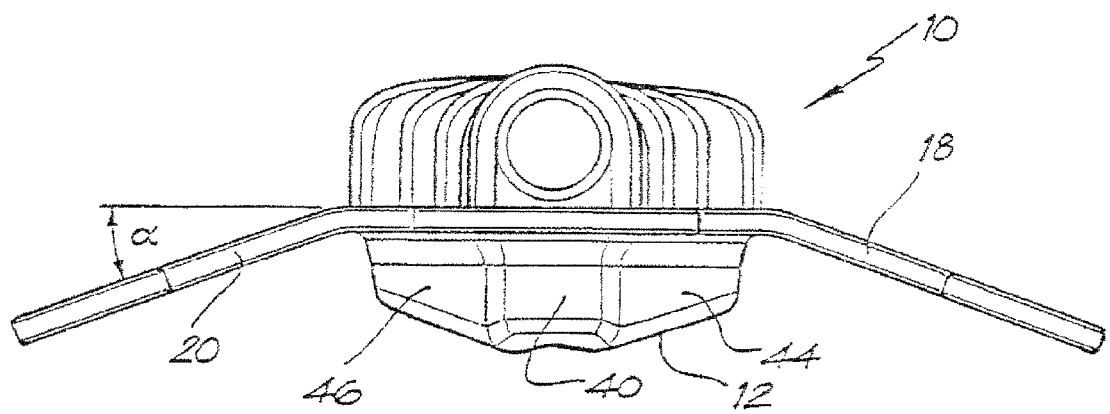
FIG. 3 is a top view of the mask shown in FIG. 1.
Figure 4:
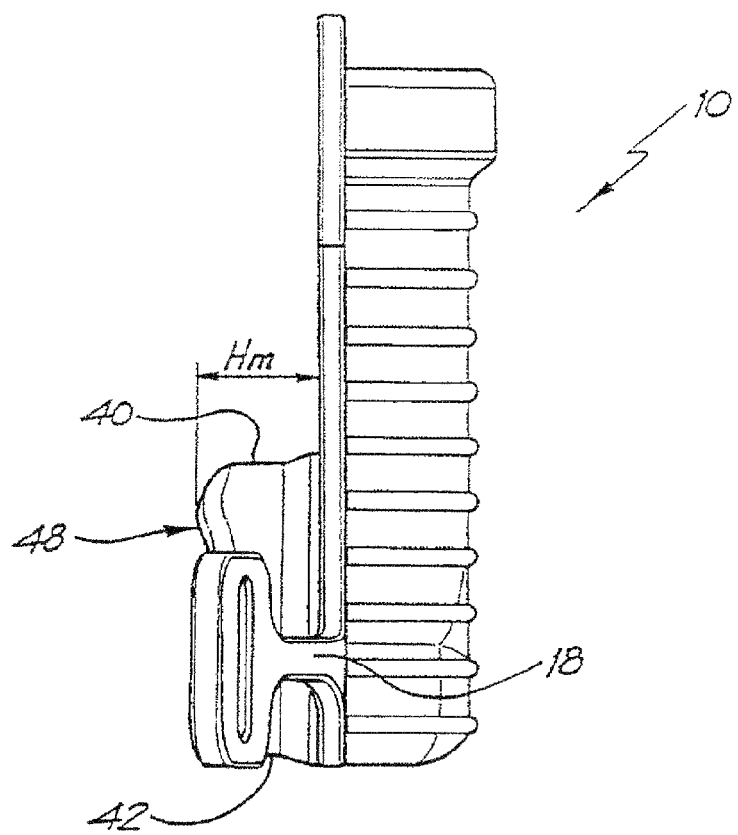
FIG. 4 is a side view of the mask shown in FIG. 1.

With reference to FIG. 3, it can be seen that the plane of the arms 18, 20 is offset from the plane of the triangular backing plate by an angle alpha of around 20°. This offset is best seen in FIG. 3. Thus when the mask 10 is located on an infant's face the arms 18, 20 extend down towards the infant's cheeks so that the mask 10 has a low profile and tends to fit better and is less likely to be dislodged during sleep.

The shaped membrane structure 12 is generally trapezoidal in cross section and is glued to (or may be integrally moulded with) the perimeter of the triangular backing plate. It comprises a thin silastic membrane and as seen oriented in FIG. 2 has four walls, namely a top 40, a base 42, and sides 44 and 46. As can be seen in FIG. 3 the walls extend away from the triangular backing plate, with the sides 44 and 46 tapering inwardly generally at an angle of approximately 70 to 80° relative to the plane of the backing plate.

The height of the membrane Hm above the backing plate is approximately 12 mm (although this height may vary from 7 mm upwards depending on the size of the infant human) and the height is not constant as the front face 48 of the membrane structure is contoured. The sides of the membrane vary in thickness from about 1.2 mm where the structure joins the backing plate to about 0.2 mm at the front face 48. This is best seen in the section, FIG. 7.

Figure 8:
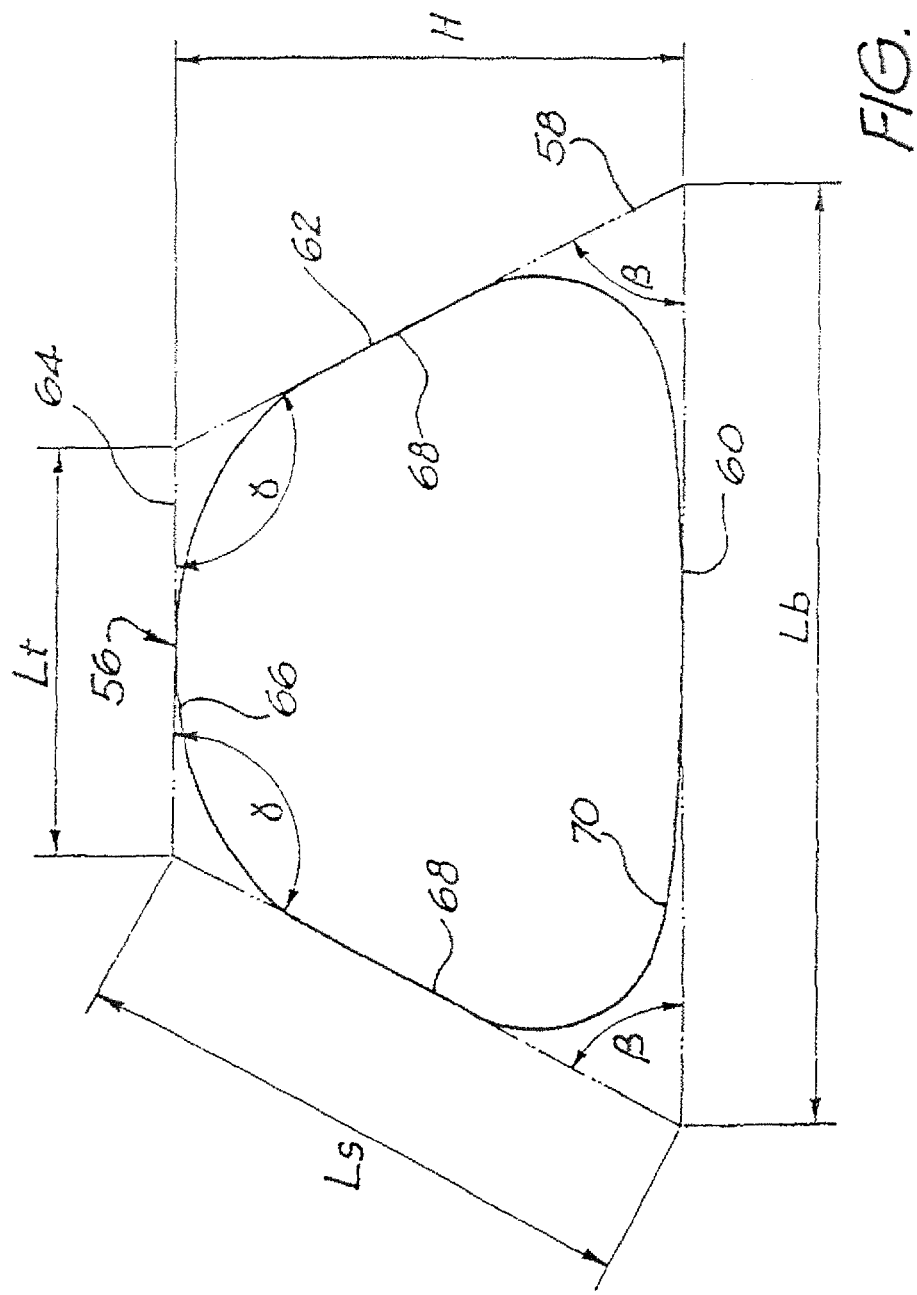
FIG. 8 shows the shape of an opening in the mask of FIG. 1.

A generally trapezoidal aperture 56 is defined in the front face 48 of the membrane structure 12. The shape and size of the aperture 56 is shown schematically in FIG. 8 located inside a notional isosceles trapezium 58 shown in phantom which touches the sides 68, top 66 and base 70 of the aperture, although the membrane may be scaled up or down depending on the age/size of the infant for which the mask is made and the proportions may be varied whilst still retaining the benefits of the invention. The isosceles trapezium 58 has a base 60 with length Lb, sides 62 with lengths Ls and a top 64 with length Lt. The top 64 is tangential to the symmetrically curved top 66 of the aperture 56. As shown, the sides 62 are an extension of a central straight line portion of the aperture's sides 68, although if these sides 68 were curved only and did not define a straight portion the sides 62 would be tangential to the aperture sides 68 at the centre point of the aperture sides 68. Likewise the base 60 is an extension of a central straight line portion of the aperture base 70, although if the aperture base 70 was symmetrically curved only and did not define a straight portion would be tangential to the curved aperture base at the centre point of the aperture base 70. In a mask for 3 month old infants the angle beta between the base 60 and the sides 62 of the trapezium 58 is about 62 degrees (but may be from 55 to 65 degrees). The length Lb of the base 60 is about 31 mm. The height H of the trapezium 58 is about 17 mm. The length Ls of the sides 62 is about 19 mm and the length Lt of the top 64 is about 14 mm. The angle gamma between the top 64 and the sides 62 is 118 degrees (but may be from 115 to 125 degrees).

For a mask for a typical twelve month old infant the generally trapezoidal aperture 56 in the membrane 12 will have a base of around 40 to 45 mm long and a height of around 18 to 25 mm and a top which is approximately 18 mm long and which is preferably slightly curved.

The ratio Lt to Lb is in the described embodiment 1 to 2.4, although it is envisaged that ratios of between about 1 to 1.8 to about 1 to 3 could be used.

As used herein, the term a "generally trapezoidal aperture" is defined as an aperture which can be fitted to typically within but also possibly outside a unique isosceles trapezium, the sides, top and bottom, of which trapezium are either extensions of the centre of the sides, top and bottom respectively, of the aperture, or tangential at their centre points to the sides, top and bottom respectively, of the aperture and in which the length of top Lt of the trapezium is from five ninths to one third of the length of the base Lb of the trapezium. It is to be noted that the definition uniquely describes the shape of the isosceles trapezium. If the sides, top and base of the aperture are all generally convex it will be appreciated that the aperture will be located within the isosceles trapezium. In contrast, if the sides, top and base of the aperture are all generally concave the aperture will be located outside the isosceles trapezium. If some of the sides top and base are convex and some concave, the aperture may straddle and partly overlap the isosceles trapezium.

The rim or edges of the aperture 56 define the contact area around the nasal area of an infant, in use. As can be seen the upper edge 66 of the aperture 56 which contacts the bridge of the nose of the infant is curved. The side edges 68 are generally straight although the corners where they meet the upper edge 66 and the lower edge 70 are rounded. The lower edge 62 where, in use, the structure contacts the skin area below the nares and above the infant's top lip is longer than the upper edge 66 and is also curved but more gently than the upper edge 66.

Figure 9:
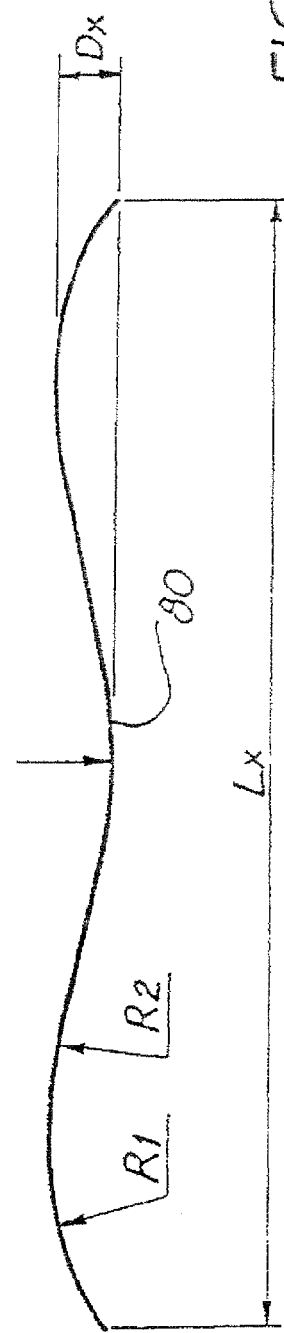
FIG. 9 illustrates a first contour generated for shaping the infant mask of FIG. 1.
Figure 10:
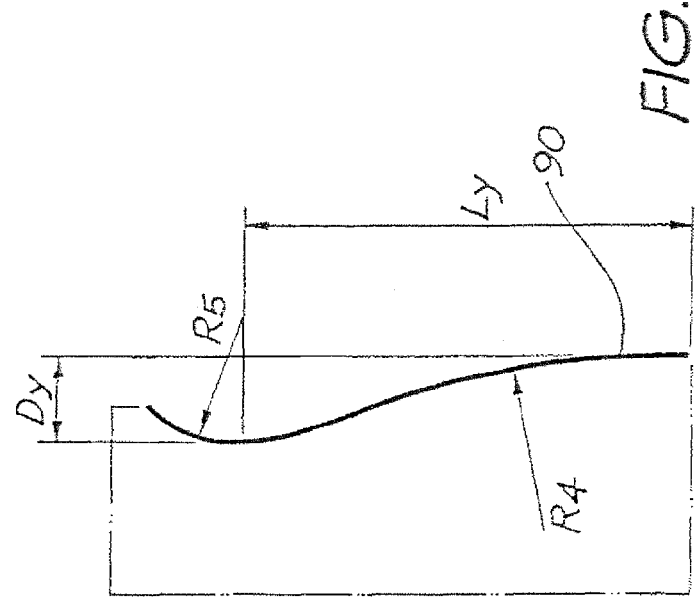
FIG. 10 illustrates a second contour generated for shaping the infant mask of FIG. 1.

As well as having an aperture 56 which is optimised to suit an infant the front face 48 of the membrane structure is also contoured to suit an infant. The described embodiment is for a three month infant. FIG. 9 illustrates an "x-axis" contour line or spline curve 80 which is used in conjunction with a Y axis contour line/spline curve 90 to simulate the shape of a typical infant's facial contours. The length Lx of the curve 80 is 42 mm and the radii R1, R2 and R3 as shown of the curve 80 are 11.6 mm, 46.2 mm and 17.70 mm, respectively. The depth Dx of the curve between the apices is 2.2 mm. The curve simulates the contour across an infant's face. For the y axis curve 90 shown in FIG. 10, R4 is 62.4 mm, R5 is 8.0 mm, the depth Dy of the curve between apices is 5.4 mm and the length Ly of the curve between the apices is 27.0 mm. Clearly the shapes of the curves 80, 90 can be varied from the described embodiment whilst still retaining the benefits of the invention.

Figure 11:
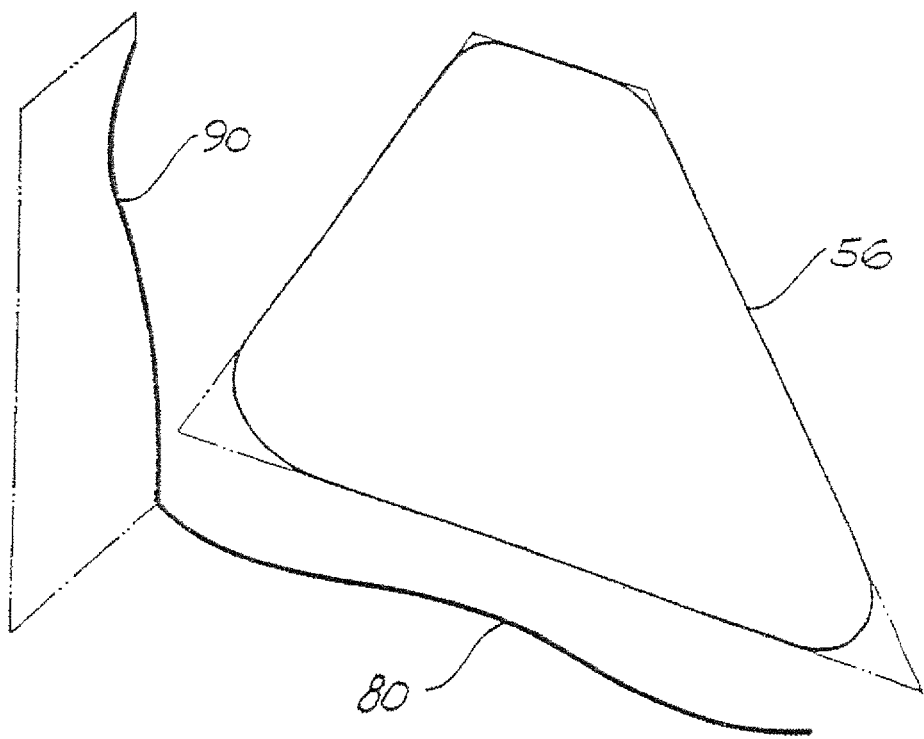
FIG. 11 illustrates a contour geometry representing an infant's facial surface used in the design of the infant mask of FIG. 1.

FIG. 11 illustrates the use of the curves 80 and 90 to contour the front face 48 of the aperture profile 56 with contour 90 being swept along contour 80. This creates an appropriate bubble to infant contact surface that does not rely significantly on flexing or deformation of the membrane structure to achieve a good seal and a comfortable fit. It is also possible to have a generally flat front face 48 as shown in the variant illustrated in FIG. 13 for example. The silastic material is such that when air is supplied at the aperture 56 it forms a hermetic seal by distending the membrane 12 and enhancing the form of the membrane 12 to the facial contours of the infant.

Figure 16:
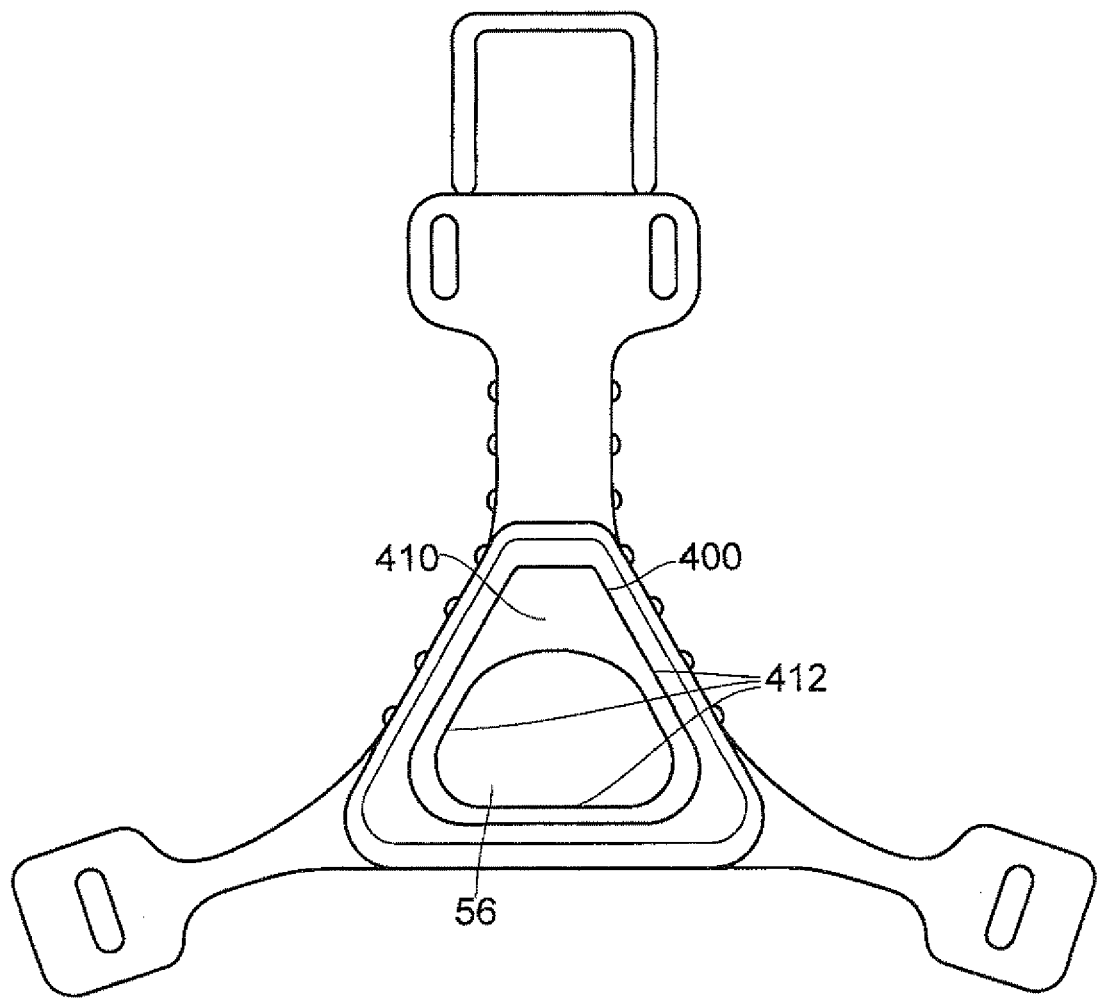
FIG. 16 is a front pictorial view of a mask outlining a generally planar face contacting portion of the mask.
Figure 17:
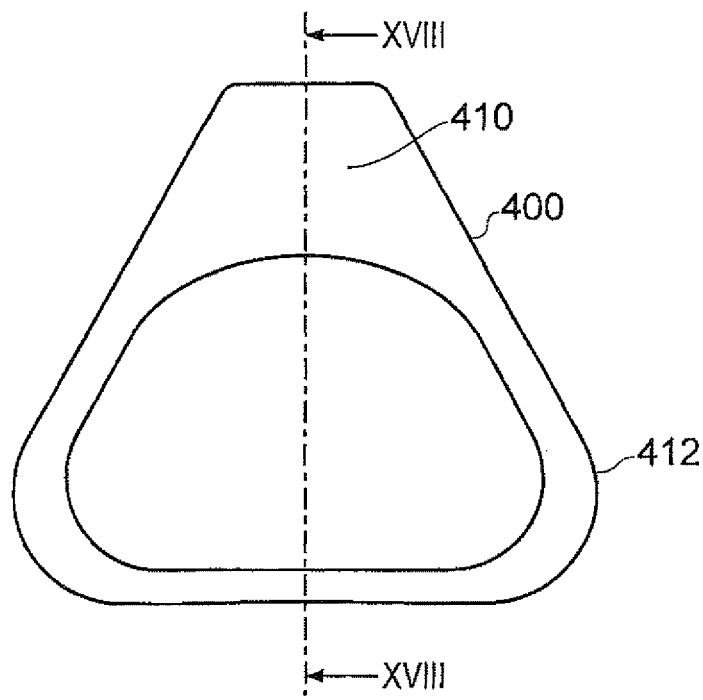
FIG. 17 is an enlarged view of the face contacting portion.

With particular reference to FIGS. 16 to 20, it will be noted that although the face contacting portion 400 of the membrane is contoured, the membrane is significantly flatter than a typical adult face mask. FIGS. 16 and 17 illustrate a face contacting portion 400 of the mask surrounding the aperture 56. The face contacting surrounding portion 400 extends from between approximately 4 mm (for very small masks for premature infants) to about 10 mm in relatively larger masks for 9 to 12 month old infants, out from the top edge of the aperture 56 shown at 410. The face contacting surrounding portion 400 extends from between approximately 1 mm (for very small masks for premature infants) to about 3 mm in relatively larger masks for 9 to 12 month old infants, out from the sides and bottom edges of the aperture 56 shown at 412.

Figure 18:
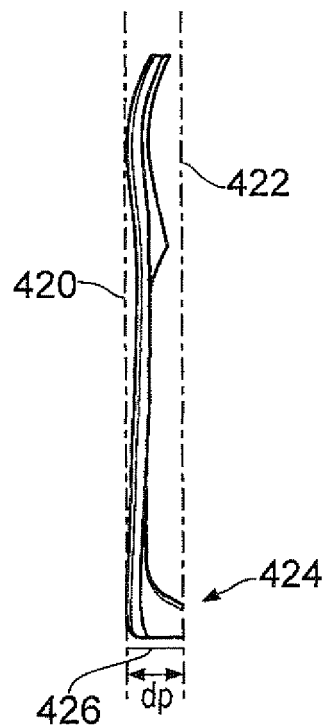
FIG. 18 is a section on XVIII-XVIII of FIG. 17 with two parallel lines illustrating the maximum difference in height of a membrane surface from a plane.
Figure 19:
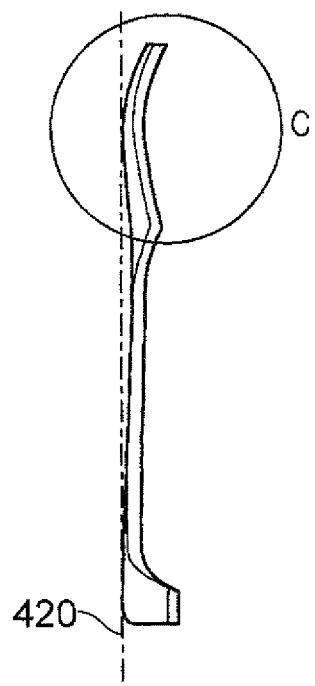
FIG. 19 shows a cross section of the planar face contacting portion.
Figure 20:
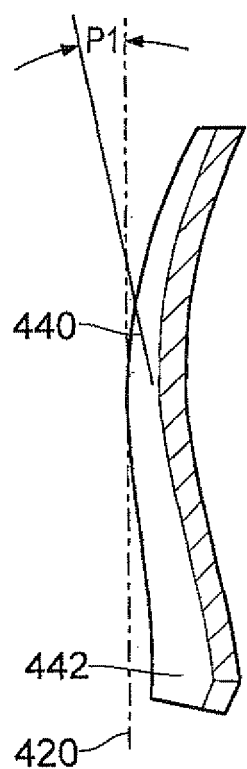
FIG. 20 is a detail of the part C of the cross section shown in FIG. 19 illustrating the surface curvature of the shaped membrane.

FIGS. 18 to 20 illustrate the sectional shape of the surrounding face contacting portion. In particular FIG. 18 illustrates the surrounding face contacting portion sandwiched between two planar surfaces 420 and 422. The planar surface 420 is a planar surface which touches the front of the surrounding face contacting portion. The planar surface 422 is a parallel surface to surface 420 which includes the farthest point 424 of any part of the surrounding face contacting portion extending from the planar surface 420. The maximum distance $d_p$ between the surfaces 420, 422 shown at 426 is less than 5 mm.

FIGS. 19 and 20 illustrate the surface curvature of the face contacting portion 400. The surrounding face contacting portion 400 is again shown in contact with the planar surface 420. FIG. 20 shown a detail of portion C of FIG. 19 enlarged. A line 440 has been drawn tangential to the front face of the surrounding face contacting portion 400 and perpendicular to the mask aperture 442 at the point of cross section. The angle $P_1$ between the planar surface 420 and the plane containing the tangent 440 is less than 20 degrees at all points around the surface.

The shape of the aperture provides for a good fit over the nasal area of an infant and allows for unimpeded breathing of air by that infant. Further the thickness of the sides of the membrane at the backing plate, the inwards tapering of the sides and the shape of the membrane structure generally, gives the membrane structure the necessary rigidity which is necessary for it to function and maintain its shape. It is important that when the device is placed over an infant's nose, the membrane structure has sufficient strength and rigidity to prevent it collapsing under the weight of the backing plate and any air or oxygen tubes attached thereto. However the membrane can still be as thin as 0.2 mm at the infant's face to enable it to mould to the shape of that infant's face around its nose if necessary.

Figure 5:
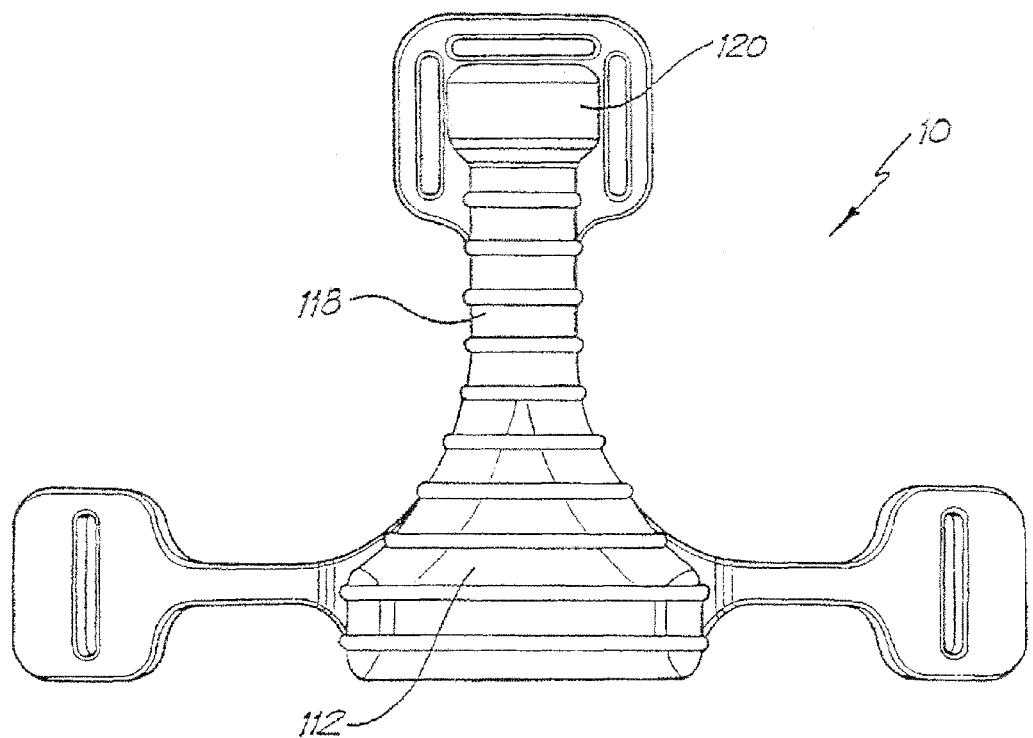
FIG. 5 is a rear view of the mask shown in FIG. 1.
Figure 6:
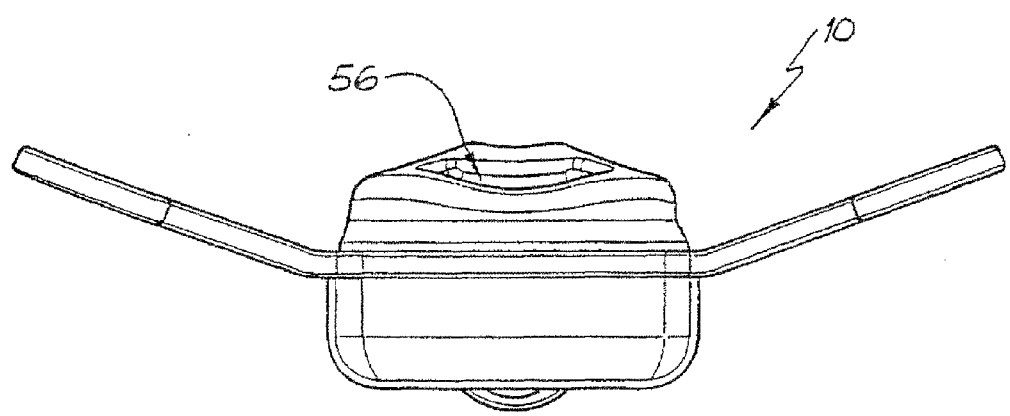
FIG. 6 is an bottom view of the mask shown in FIG. 1.
Figure 7:
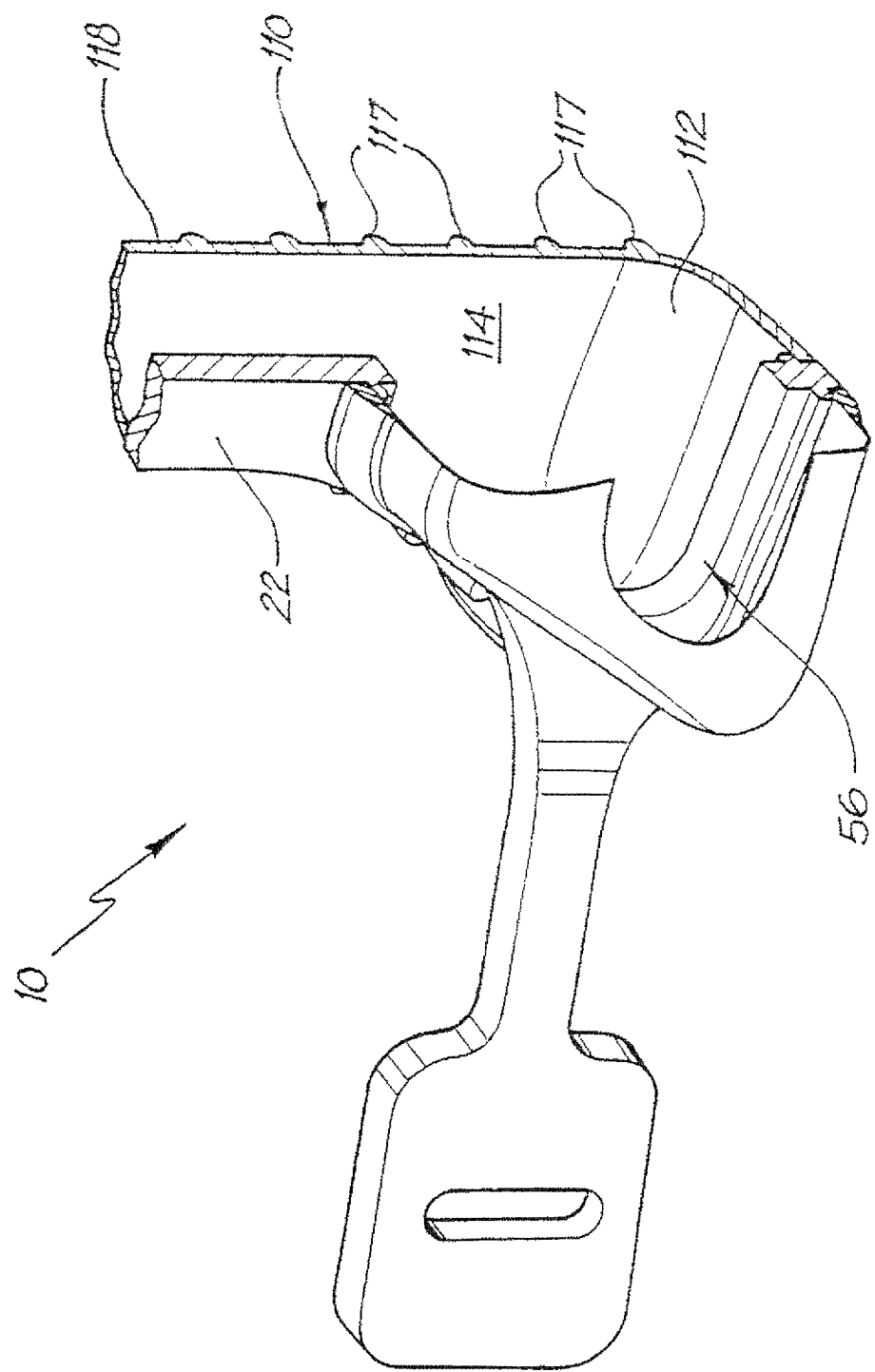
FIG. 7 shows a section cut through the centre of the mask of FIG. 1, showing the lower part of the mask only.

The manifold 16 is best seen in FIGS. 5 and 7. It includes a generally triangular portion 112 with a back 114 and an open face which is in fluid communication with the membrane structure and aperture 56. A channel portion 118 extends away from the triangular portion 112. The manifold 16 is formed from a thin membrane approximately 1 mm thick reinforced with a series of thicker ribs 117. The manifold is glued to the reverse side of the support structure 14 in a gastight fashion as is best seen in FIG. 7. The arm 22 and channel 118 combine to form a pipe leading from the distal end of the arm 22 to the centre of the mask. An air inlet port 120 is defined at the end of that pipe. Pressurised air travels down the pipe through an aperture in the support structure into the membrane structure and out via the aperture 56. The manifold 110 also includes a number of small holes (not shown) which allow the leakage to atmosphere of expired air.

The structure formed from the membrane and strengthening ribs allows the arm to flex but at the same time, maintain the integrity of the manifold. The upper pad can be anchored to the forehead of the infant with the air delivery pipe attached. The torsion acting on the mask due to the pipe is concentrated at this point. This has substantial benefits, as it reduces the amount of torsion acting on the mask and helps leakage of the face mask in use.

Figure 12:
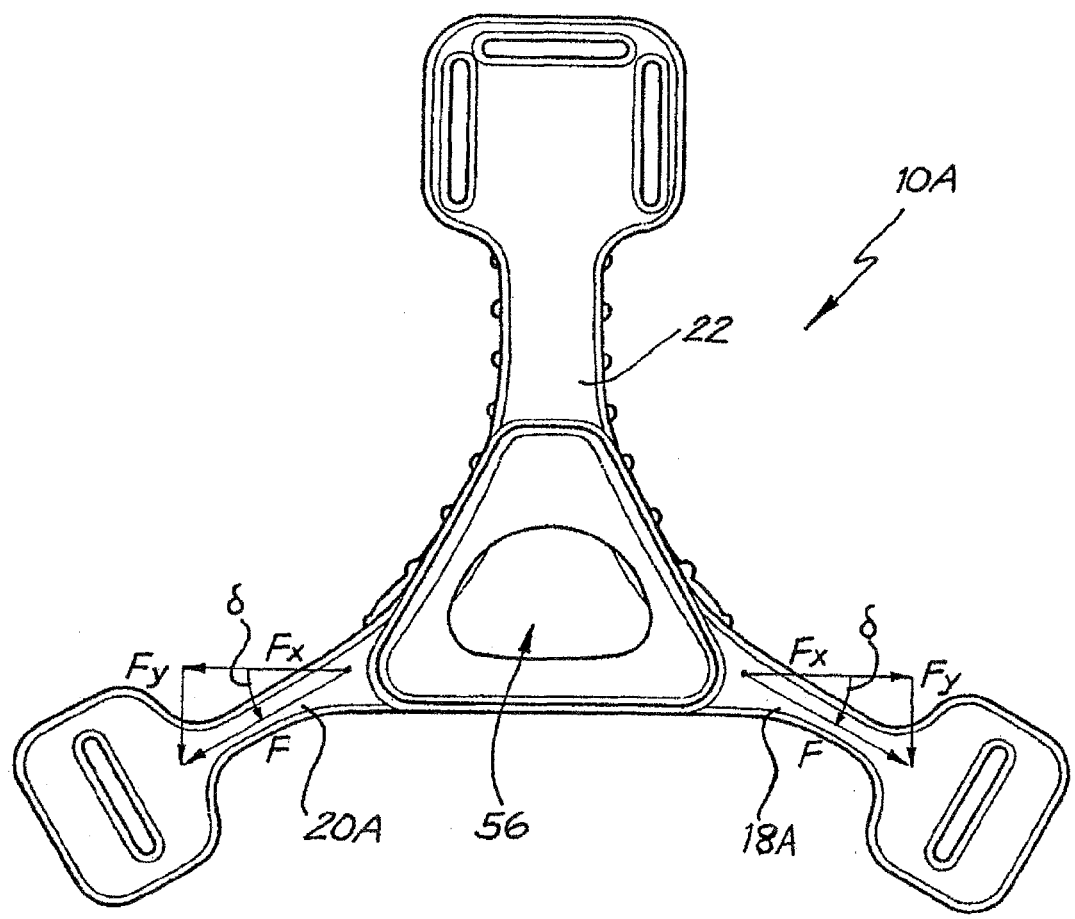
FIG. 12 is a front view of a second embodiment of a mask to fit the nasal area of a three month old infant.

FIG. 12 shows a variant 10A of the mask of FIG. 1 in which the lower arms 18A and 20A do not extend generally parallel to the base of the triangular plate but are angled downwardly. This enables the pads to locate lower down on an infant's face which generally provides a better fit than the mask of FIG. 1. Forces F acting along the arm 20A provide a force vector Fy downwards as well as a vector Fx across the infant's face (when the strap is attached to a head harness). The vector Fy tends to pull the mask down from the nose bridge preventing the mask from moving up in that direction. This is an important advantage because infants tend to move their head from side to side tends to cause existing masks to ride up the infant's face towards their forehead. As illustrated the angle delta between the base of the mask and the angle of the arms is about 30 degrees and may preferably be about 20 degrees to about 40-45 degrees.

FIGS. 13 and 14 show a further variant in which a mask 200 is separable into two parts, an "applicator" 202 and a manifold 204 best seen in FIG. 14. The applicator is similar to the front part of the mask of FIG. 1 except that the front face 206 of the membrane structure is flat. The rear of the mask is different since air is supplied via the detachable manifold 204.

The manifold 204 includes a circular chamber 208 having at least one connector port 210, the specific embodiment having two opposed connector ports 212, one of which is normally closed with a bung, in use. The connector ports 212 allows the attachment of an air delivery pipe. The chamber 208 defines an open end from which an annular cylinder projects and defines an external flange which is shaped and configured to engage behind an internal flange of the applicator 202 for uses in connecting the manifold 204 to the applicator 202. Other connection means could be used.

In use, the applicator may be used without the manifold in place on an infant to train the infant to use a mask and to acclimatise the infant to the feel of a mask on there face without the manifold and tubes which are bulky. The use of nasal CPAP or nasal ventilation or nasal pressure support systems in infants, often requires a period of training in which the infant or child is allowed to wear part of a mask at bed time, and during sleep, before any attempt is made to introduce the air flow and pressure source. The mask system of the present invention allows for this in a very satisfactory manner since the use of the applicator alone will not impede the flow of air to the infant. The applicator may be stuck to a child's face by applying skin adhesive such as elastogel or Duo Derm (manufactured by Convatec Bristol Myers Squibb) over the pads 32. Alternatively, the pads could define further attachment means for connecting to straps attached to a cap.

Further, the infant or child can be allowed to go asleep with only the applicator attached without the presence of air pressure and air flow coming into the nasal region, but when asleep, the carer or parent can then snap fit the manifold to the applicator so completing the formation of a fully operational CPAP mask, or pressure support ventilation mask. Typically in use, the system should provide fresh air at a mask pressure of approximately 5 mm water.

In a variation (not illustrated) either one of a hole in the applicator or a projection from the manifold is generally elliptical so that compression of the ellipse into a circle can be used for inserting the projection into the hole such that when the ellipse is relaxed, it will return to its original shape and retain the projection in the hole.

FIG. 15 illustrates the mask 10A shown in FIG. 12 attached to a harness 300. The FIG. 15 illustrates the force vector Fy along the arm 20A pulling the mask down the infant's face. Infants move their heads from side to side in sleep, since they are not strong enough to lift their heads and in existing masks which do not provide the downwards vector, this movement causes the mask to ride up the infant's forehead.

One advantage of the embodiments of the present invention, is that the applicator fits to an infant's face mostly and through its flexibility can effectively approximate to the infants facial structures. By fitting more closely and in particular, since the depth of the shaped membrane is quite shallow, the height of the mask above the infant's face is minimised and this reduces the fulcrum effect which is a particular problem with the prior art systems described above. Reducing the fulcrum effect is particularly important with infants, as they firstly tend to move around in their sleep a lot more than adults, and secondly are incapable of readjusting their mask if the mask leaks.

All embodiments of the present invention allow easy connection and disconnection from an air delivery system.

Although the embodiments of the present invention have been described as comprising a mask made of silastic, it should appreciated that it would be possible to use other elastomeric materials which have similar properties to silastic.

Whilst the masks described in the specific description are predominantly configured for a 3 month old infant, the design is such that by selecting the size of the square upon which the mask is based, a wide range of mask sizes can be created that will readily accommodate the continual growth and change in facial measurement during the first two years of life. Further it would also be possible to use various of the features of the infant masks described above in masks for older children and even adults.

The fact that all the components of the mask are made from silastic or other flexible elastomeric material increases the comfort of the mask and avoids the problem of the prior art where rigid components of the mask such as the manifold may impact or press into or onto a patient's face, in use. In addition the mask is flexible enough to enable it to distort if pressed against a rigid surface while still maintaining a tight gas seal. This ability further improves comfort and additionally reduces the likelihood of the infant casing gas leakage when moving around. In its single piece silastic format the mask is also easier to clean and may even be washed in a dishwasher.

While the masks described above will typically have the shape and characteristics defined above both in use and when not is use, it will be appreciated that the mask may not have particular shape characteristics when not in use, but be sufficiently flexible to adopt/change to that shape when in position on an infant's face.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A mask for supplying gas under pressure to the nasal airway of an infant human, including;
   a manifold for supplying air to an aperture in the mask;
   a support structure for supporting the manifold;
   a shaped membrane structure formed from a thin walled membrane extending generally away from the support structure having a front face, the shaped membrane structure defining an enclosure for receiving at least the nares of an infant human nose; and
   an aperture which is a generally trapezoidal aperture, the aperture being formed in the front face and having a top, first and second sides and a base adapted to fit around the nasal area of the infant human;
   wherein the generally trapezoidal aperture is bounded by a notional isosceles trapezium that is defined by a straight top line, first and second straight side lines and a straight base line,
   wherein at least a portion of the top of the aperture is coincident with at least a portion of the to line of the isosceles trapezium, at least a portion of the first side of the aperture is coincident with at least a portion of the first side line of the isosceles trapezium, at least a portion of the second side of the aperture is coincident with at least a portion of the second side line of the isosceles trapezium, and at least a portion of the base of the aperture is coincident with at least a portion of the base line of the isosceles trapezium;
   wherein the top line and base line of the isosceles trapezium each have a length and the length of the top line of the isosceles trapezium is between about five ninths to one third of the length of the base line of the isosceles trapezium and
   wherein at least a portion of the membrane of the front face adjacent the top of the trapezoidal aperture is generally planar while other parts of the membrane around the aperture are sufficiently flexible to mould to the shape of the infant human's nasal area or are contoured to generally match the contours around that nasal area whilst the membrane structure itself has sufficient rigidity to support the weight of the support structure without collapsing.

2. A mask for supplying gas under pressure to the nasal airway of an infant human as claimed in claim 1, wherein the angle between the first and second side lines and the base line of the isosceles trapezium is from 55 to 65 degrees.

3. A mask for supplying gas under pressure to the nasal airway of an infant human as claimed in claim 1 wherein the angle between the first and second side lines and the top line of the isosceles trapezium is from 115 to 125 degrees.

4. A mask as claimed in claim 1, wherein the mask adopts a shape such that the aperture maintains the generally trapezoidal shape in use, in situ on the infant's face.

5. A mask as claimed in claim 1, wherein the manifold, support structure and shaped membrane structure are all formed from a flexible or elastomeric material.

6. A mask for supplying gas under pressure to the nasal airway of an infant human as claimed in claim 5, further including at least three arms and wherein the mask including the manifold, support structure, shaped membrane structure and arms is moulded in one piece.

7. A mask as claimed in claim 1, wherein the membrane defines a contact area which is profiled or contoured to approximate to the profile of an area of an infant's face surrounding said infant's nares.

8. A mask as claimed in claim 1, wherein the length of the top line of the isosceles trapezium is about five twelfths of the length of the base line of the isosceles trapezium.

9. A mask as claimed in claim 1, wherein the thickness of the membrane diminishes from the support structure to the aperture.

10. A mask as claimed in claim 9, wherein the membrane is about 0.8 to 1.2 mm thick adjacent the support structure and about 0.2 mm thick at the aperture.

11. A mask as claimed in claim 1, wherein the support structure is flexible and generally planar.

12. A mask as claimed in claim 1, further including three flexible arms each arm defining a pad distal from the aperture and wherein the pads, arms and membrane are all integrally moulded from a flexible elastomeric material.

13. A mask as claimed in claim 12, wherein the flexible elastomeric material is a high tear resistant silicone elastomer.

14. A mask as claimed in claim 12, wherein two of the arms are adjacent a base of the mask and extend along a plane that is offset from a plane of the support structure by around 10 to 25°, such that when the mask is placed over the nasal area of an infant human the arms tend to extend downwardly onto the cheeks of the infant.

15. A mask as claimed in claim 1, wherein the mask is provided in two detachable parts.

16. A mask as claimed in claim 1, wherein the manifold comprises of a thin flexible material and includes a series of hoops or strengthening rings to assist the membrane in maintaining the shape of the manifold.

17. A mask as claimed in claim 1, wherein the generally trapezoidal aperture defines corners which are rounded and wherein the top of the generally trapezoidal aperture, is slightly curved.

18. A mask as claimed in claim 1, wherein the membrane structure defines a surrounding portion that has a front, the surrounding portion enclosing the aperture and extending a distance of at least 1 mm from the sides and base of the aperture and at least 4 mm from the top of the aperture, and
   wherein the surrounding portion of the membrane is generally flat such that measured against a plane touching the front of the surrounding portion the distance of a furthest point of the surrounding portion is 5 mm.

19. A mask as claimed in claim 18, wherein the surrounding portion enclosing the aperture extends a distance of 4 mm from the sides and base of the aperture and 10 mm from the top of the aperture.

* * * * *